(12) United States Patent
Farkas et al.

(10) Patent No.: US 6,521,764 B1
(45) Date of Patent: Feb. 18, 2003

(54) PROCESS FOR THE PREPARATION OF FUMAGILLIN

(75) Inventors: Gyula Farkas, Budapest (HU); Andrea Györbiró, Budapest (HU); István Hermecz, Budapest (HU); Kálmán Simon, Budapest (HU); Anna Szabó, Budapest (HU); ÁrpádnéVasvári, Budapest (HU)

(73) Assignee: Sanofi-Synthelabo, Paris (FR)

( * ) Notice: Subject to any disclaimer, the term of this patent is extended or adjusted under 35 U.S.C. 154(b) by 19 days.

(21) Appl. No.: 10/009,116

(22) PCT Filed: Jun. 6, 2000

(86) PCT No.: PCT/HU00/00054

§ 371 (c)(1),
(2), (4) Date: Mar. 5, 2002

(87) PCT Pub. No.: WO00/76994

PCT Pub. Date: Dec. 21, 2000

(30) Foreign Application Priority Data

Jun. 11, 1999 (HU) ............................................... 9901943

(51) Int. Cl.$^7$ ............................................ C07D 305/14

(52) U.S. Cl. ....................................................... 549/332
(58) Field of Search .................................. 549/332, 337

(56) References Cited

U.S. PATENT DOCUMENTS 5,328,930 A    7/1994  Wilson ........................ 514/475

FOREIGN PATENT DOCUMENTS

| AT | 193 076 | 11/1957 |
| DE | 36735 | 2/1965 |
| DE | 1 901 483 | 10/1969 |

OTHER PUBLICATIONS

Derwent Patent Abstract Nos. 197010 and 196800 (2001).

*Primary Examiner*—Ba K. Trinh
(74) *Attorney, Agent, or Firm*—Michael D. Alexander; Paul E. Dupont

(57) ABSTRACT

The invention relates to a process for the preparation of Fumagillin by liberation from its salt characterized by reacting Fumagillin dicyclohexylamine salt with an organic acid in alcoholic medium. According to the process Fumagillin can be produced in high yield and pure condition and with higher stability than products obtained by other preparation methods

15 Claims, No Drawings

PROCESS FOR THE PREPARATION OF FUMAGILLIN

This application is a 371 of PCT/HU00/00054 filed Jun. 6, 2000.

Process for the preparation of Fumagilhn Fumagillin of the formula (1), a fermentation product of Aspergillus fumigata, is a potent antimicrosporidial agent. In its stable dicyclohexylamine salt form it is used in the veterinary medicine against microsporidiosis of bee and fish (Fumidil, Fumadil B, Amebicillin, etc).

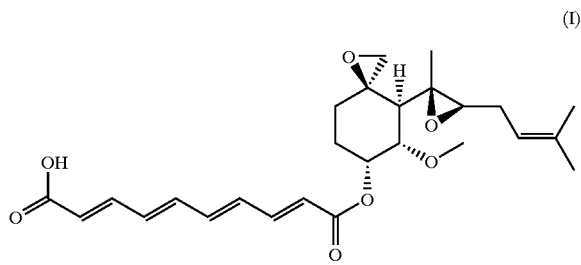

(I)

Fumagillin was recently found to be potent to cure intestinal infections caused by Microsporidia and/or Cryptosporidia in man (WO 96/30010). These infections are deadly diseases for patients with immunodeficiency.

Fumagillin, the monoester of decatetraenedioic acid and Fumagillol, is a very sensitive material. Due to its reactive groups (two epoxide groups capable for hydroxylation and ring opening; conjugated polyene-chain capable for dimerisation, polymerisation, epoxidation, hydroxylation; ester group capable for hydrolysis), Fumagillin is very sensitive to heat, air, light, acids, bases. It is considered to be stable at -80 ° C.

Fumagillin gives stable salts with amines containing bulky cycloalkyl substituents, like cyclohexylamine or dicyclohexylamine (the latter is used in the veterinary medicine). However, these amines are pharmaceutically not accepted in the human medicine as salt forming components, since they can accumulate in the tissues due to their lipofilic character. In addition, the Fumagillin dicyclohexylamine salt used in the veterinary medicine is of a purity of only 85%. (This means a Fumagillin content of only 61%).

To obtain Fumagillin, appropriate as a drug substance for human treatment, we aimed to prepare Fumagillin in pure form from the commercially available Fumagillin dicyclohexylamine salt, by a method which is also suitable for scaling-up. Purification of Fumagillin by recrystallization -subsequent to the liberation- is possible in small amounts, but it is not advisable in larger quantities, because of the sensitivity of the material to heat. Therefore, it was essential in our effort to obtain Fumagillin in pure condition directly from the liberation process, without further purification.

There is no reference to find in the literature for the preparation of pure Fumagillin from its salts.

The common method to obtain organic acids from their salts is liberation of the acid in aqueous medium by an inorganic or organic acid. As Fumagillin is sensitive to acids we used milder organic acids, i.e alkanecarboxylic acids of pKa 4.7 - 4.9 , in excess amount.

We carried out the liberation of Fumagillin from its dicyclohexylamine salt. with excess amount of acetic acid (pKa 4.76). The temperature of the aqueous reaction mixture was carefully maintained between 0-(+5) ° C. The precipitated Fumagillin, however, was not pure enough. It was therefore extracted with dichloromethane, the dichloromethane phase was washed with water, dried, concentrated in vacuo, and Fumagillin was precipitated from the concentrated solution on addition of methanol. The product thus obtained was pure, but it contained residual dichloromethane in high amount. The whole process was tedious, long and not appropriate for scaling-up. Yields varied between 45-60%, yields and also the quality of the product was not well reproducible.

To avoid the disadvantages of the above method we tried, liberations by alkanecarboxylic acids in organic media. Liberation in toluene was successful, however, dissolution of the salt on the effect of the acid was immediately followed by the precipitation of Fumagillin, allowing no possibility for a filtration, although filtration may be important. The product was not as pure as desired and its residual toluene content was high. Next we tried liberations in solvents or solvent mixtures of various ratio with the criterium, that a filtration has to be carried out during the process. We tried solvents such as toluene, alcohols, dichloromethane, acetonitrile, dioxane, acetone, ethyl acetate and their binary mixtures . Yields were medium to good. Residual solvent content of the products were also investigated.

The subject of our invention, in accordance with the above is a process for the preparation of Fumagillin by liberation from its salt characterized by reacting Fumagillin dicyclohexylamine salt with an organic acid in alcoholic medium. As organic acids, alkanecarboxylic acids with a pKa value of 4,7-4,9, preferably acetic acid, propionic acid, as alcoholic medium methanol, ethanol or propanol can be used The organic acid is preferably used in excess.

As a result of our process we have found that liberations in alcoholic medium gave surprisingly favourable results. The solution of the salt could be filtered, the acid was liberated from the clear solution. Yields were good, the product was pure. Residual solvent content in case of an alcohol is not critical, however, it is favourable that the products contained very little residual solvent. The process itself was mild, fast and well reproducible.

The most surprising result was that the Fumagillin samples obtained by this alcoholic method - probably due to their purity and low residual solvent content - turned out to be considerably more stable than the samples obtained by other methods. We carried out a 2-week stability study at 40 OC , ambient humidity, of selected samples obtained by various methods. The Fumagillin content of the samples was measured by HPLC before and after the stressing. Some demonstrative results are presented in the table below.

For liberation 3 equivalent of acetic acid were used in all demonstrated cases.

| Method of Prepartion Liberation from: | HPLC Assay | | Residual Solvent content/ppm/ | |
|---|---|---|---|---|
| | Initial | After 2 weeks at 40° C., ambient humidity | /Class 2 Solvents/$^x$ | Σ Solvent |
| Aqueous medium/ followed by extraction with dichloromethane, concentration and crystallization in methanol/ | 96.9% | 54.9% | dichloromethane 1200 | 1743 |
| Toluene/ crude product/ | 92.6% | 61.0% | Toluene 3000 | >3000 |
| Methanol- | 96.3% | 49.9% | Dichloro | 1518 |

| Method of Prepartion Liberation from: | HPLC Assay | | Residual Solvent | |
|---|---|---|---|---|
| | Initial | After 2 weeks at 40° C., ambient humidity | content/ppm/ /Class 2 Solvents/ˣ | Σ Solvent |
| Dichloromethane 5:1/crude product/ | | | methane 1273 | |
| Methanol/ crude product/ | 97.6% | 85.1% | — | 118 |

ˣSolvents with limitation (ICH Guidelne for Residual Solvents)

Thus, we have found a method yielding Fumagillin in high yield and pure condition; in ,addition the product obtained by this method turned out to be considerably more stable than products obtained by other preparation methods. Higher stability is a significant advantage in the case of such a sensitive drug substance.

The process itself is simple, fast, well reproducible, environment friendly and also appropriate for scaling-up.

Further details of the invention are demonstrated by the following examples, without limiting the claims to the examples.

EXAMPLES

Example 1 Liberation of Fumagillin from its Dicyclohexylamine(DCH) salt in methanolic medium by 3 equivalent of acetic acid.

3.2 g (5 mmol) of Fumagillin DCH salt were dissolved in 16 ml of methanol at room temperature. The insoluble material was filtered off. To the clear filtrate 0.90 g (15 mmol) of acetic acid of 99-100% were added under stirring at room temperature. After a few minutes of stirring white fine crystalline materal started to precipitate and within 5-10 minutes a thick suspension was obtained, which was cooled in refrigerator overnight. The crystals were then filtered off, washed with cold methanol (3x 4 ml) and dried in vacuum dryer at room temperature to dryness (approx. 7 hours).
Product: white, powdery crystals, mp: 190.4- 192.3 ° C.
yield: 1.6 g (69.8%)
Purity by HPLC Area % 97.60%

| Elementary analysis: calculated for $C_{26}H_{34}O_7$ | Theoretical: | Found: |
|---|---|---|
| | C% 68.10 | 68.28 |
| | H% 7.47 | 7.68 |

Water content by Karl-Fisher: 0.16%
Residual solvent content by GC headspace: 5 Solvent content: 249
UV(in 96% ethanol): ma,=321(log 4.69), Nma,=335(log 4.88), 2w321(log s 4.69).
IR (KBrpellett): 3374 cm$^1$ /v OH, CHI; 1711 cm$^1$ /v C=O/; 163 cmrd /v C=C/; 1445,1372 cmid /6 CH$_3$, p CH$_2$ 1; 1276 cm7/v C-O-C epoxy/; 1233, 1161, 1015 cm/v C-O-C/.
MS: El Mass spectrum: M+m/z =458 [U]D$^{20}$ =-27.5° (c=l, [ethanol:methylene chloride 4:1]

Example 2

Liberation of Fumagillin from its Dicyclohexylamine salt in Methanolic medium by 4 equivalent of Acetic acid.

3.2 g (5 mmol) of Fumagillin DCH salt were dissolved in 16 ml of methanol at room temperature. The insoluble material was filtered off. To the clear filtrate 1.20 g (20 mmol) of acetic acid of 99-100% were added under stirring at room temperature. After a few minutes of stirring white fine crystalline materal started to precipitate and a thick suspension was obtained, which was treated as described in Example 1.
Product: white, powdery crystals, mp: 190.4- 192.3 ° C.
yield: 1.6 g (69.8%)
Purity by HPLC Area % 97.5%

Example 3

Liberation of Fumagillin from its Dicyclohexylamine salt in ethanolic medium by 2 equivalent of acetic acid.

3.2 g (5 mmol) of Fumagillin DCH salt were dissolved in 16 ml of ethanol at room temperature. The insoluble material was filtered off. To the clear filtrate 0.60 g (10 mmol) of acetic acid of 99-100% were added under stirring at room temperature. After a few minutes of stirring white fine crystalline materal started to precipitate and a thick suspension was obtained, which was cooled in refrigerator overnight. The crystals were then filtered off, washed with cold ethanol (3x 4 ml) and dried in vacuum dryer at room temperature to dryness (approx. 10 hours).
Product: white, powdery crystals, mp: 190.6- 192.0 OC.
yield: 1.50 g (65.4%)
Purity by HPLC Area % 97.2%

Example 4

Liberation of Fumagillin from its Dicyclohexylamine salt in methanolic medium by 3 equivalent of propionic acid.

3.2 g (5 mmol) of Fumagillin DCH salt were dissolved in 16 ml of methanol at room temperature. The insoluble material was filtered off. To the clear filtrate 1.1 1 g (15 mmol) of propionic acid of 99 % were added under stirring at room temperature. Afier a few minutes of stirring white fme crystalline materal started to precipitate and a thick suspension was obtained, which was cooled in refrigerator overnight. The crystals were then filtered off, washed with cold methanol (3x 4 ml) and dried in vacuum dryer at room temperature to dryness (approx. 9 hours).
Product: white, powdery crystals, mp: 190.6- 192.4 oc.
yield: 1.43 g (62.4%)
purity by hplc area% 97.4%

What is claimed is:
1. A process for the preparation of Fumagillin by liberation from its salt which comprises reacting Fumagillin dicyclohexylamine salt with an organic acid in alcoholic medium.
2. A process according to claim 1 wherein the organic acid is an alkanecarboxylic acid.
3. A process according to claim 2 wherein the alkanecarboxylic acid is acetic acid or propionic acid.
4. A process according to claim 1 wherein tBie alcoholic medium is methanol, ethanol or propanol.
5. A process according to claim 1 wherein the organic acid is used in excess. tease add the following new i c
6. A process according to claim 2 wherein the alkanecarboxylic acid has a pKa value of from about 4.7-4.9.
7. A process according to claim 6 wherein the alkanecarboxylic acid is acetic acid or ua propionic acid.
8. A process according to claim 2 wherein the alcoholic medium is methanol, ethanol or propanol.
9. A process according to claim 3 wherein the alcoholic medium is methanol, ethanol or propanol.
10. A process according to claim 6 wherein the alcoholic medium is methanol, ethanol or propanol.

11. A process according to claim 7 wherein the alcoholic medium is methanol, ethanol or propanol.

12. A process according to claim 2 wherein the organic acid is us ed in excess.

13. A process according to claim 3 wherein the organic acid is used in excess.

14. A process according to claim 6 wherein the organic acid is used in excess.

15. A process according to claim 7 wherein the organic acid is used in excess.

* * * * *